United States Patent [19]

Wudl et al.

[11] Patent Number: 4,745,227

[45] Date of Patent: May 17, 1988

[54] REVERSIBLE PHOTOCHROMATIC SOLID

[75] Inventors: Fred Wudl; Sherman D. Cox, both of Santa Barbara, Calif.

[73] Assignee: The Regents of the University of California, Berkeley, Calif.

[21] Appl. No.: 717,387

[22] Filed: Mar. 29, 1985

[51] Int. Cl.$^4$ .................. C07C 149/34; C07C 149/32
[52] U.S. Cl. ...................................... 568/49; 430/338;
568/52; 568/56; 568/57
[58] Field of Search .................. 568/49, 52, 56, 57

[56] References Cited

U.S. PATENT DOCUMENTS

| | | | |
|---|---|---|---|
| 3,096,375 | 7/1963 | Campbell et al. | 568/38 |
| 3,114,777 | 12/1963 | Reifschneider | 568/57 |
| 3,650,760 | 3/1972 | Gates, Jr. et al. | 568/44 |
| 3,686,331 | 8/1972 | O'Brien et al. | 568/56 |
| 3,879,472 | 4/1975 | Martin | 568/56 |
| 3,932,527 | 1/1976 | Metcalf et al. | 568/56 |
| 4,108,906 | 8/1978 | Anderson | 568/57 |
| 4,136,102 | 1/1979 | Crivello | 568/74 |
| 4,400,293 | 8/1983 | Romer et al. | 568/56 |

OTHER PUBLICATIONS

Banyu Pharmaceutical Co., Chem. Abstract 57:3363h (1962) citing Japan Patent 16,623 (1961).
S. D. Cox et al., J. Am. Chem. Soc. (1984), 106, 7131-7133, A Novel Organic Photochromic.
Smets, (1983) Adv. Poly Sci. 50: 18-44.
*Photochromism: Techniques of Chemistry*, vol. III, pp. 744-780 (Glenn H. Brown ed. 1971).

*Primary Examiner*—Mary E. Ceperley
*Attorney, Agent, or Firm*—Ciotti & Murashige, Irell & Manella

[57] ABSTRACT

New compounds having the generic formula:

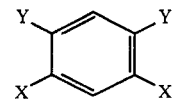

wherein:
X=halogen, Y=

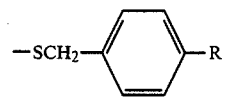

X=Y=

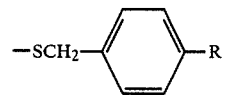

X=Y=

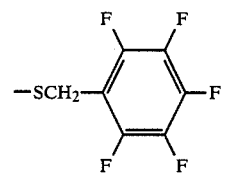

R=hydrogen, halogen such as chlorine, lower alkoxy such as methoxy, or lower alkyl such as methyl.

These new compounds are useful as reversible photochromatic solids.

7 Claims, 3 Drawing Sheets

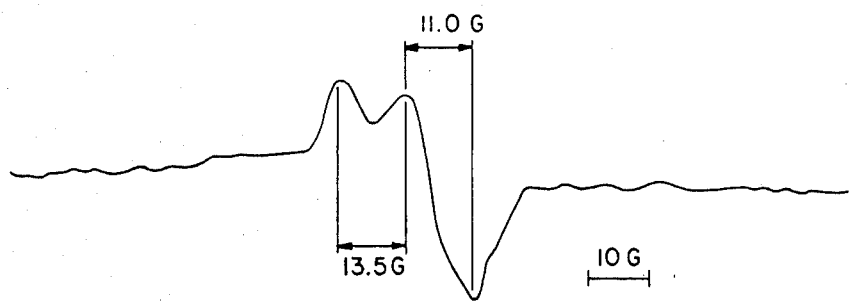
FIG. −1
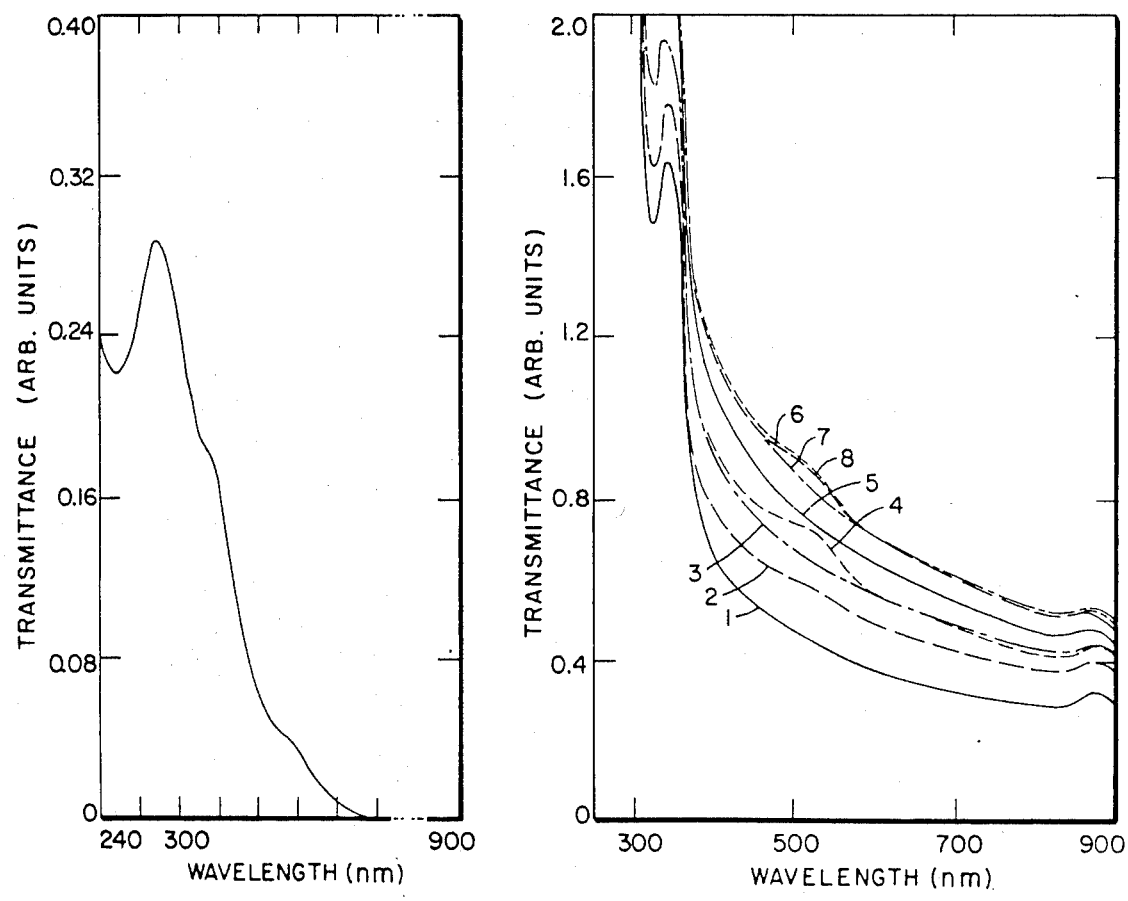
FIG. −2

REVERSIBLE PHOTOCHROMATIC SOLID

BACKGROUND OF THE INVENTION

U.S. Pat. No. 4,400,293 (Romer et al) discloses cyclohexylphenyl "derivatives" with a sulfur moiety and halogen-substituted ring. The general formula is:

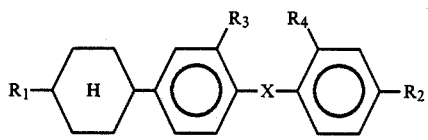

X can be S—CH₂; R₂, R₃, R₄ can be chlorine. The compounds are used as electro-optical indicators based on the changes in their optical properties under the influence of electric fields.

U.S. Pat. No. 3,650,760 (Gates, Jr., et al) discloses alkoxy mercaptophenols used in photographic silver halide emulsions in order to stabilize the emulsions.

U.S. Pat. No. 4,136,102 (Crivello) disclosed halogen onium salts which exhibit unusual activity under UV light and can be employed as cationic photoinitiators.

U.S. Pat. No. 3,932,527 (Metcalf et al) which discloses the preparation of p-p′ Disubstituted diaryl trichloroethanes for insectidal purposes.

U.S. Pat. No. 3,114,777 (Reifschneider) discloses Tolylbisthioethers of general formula:

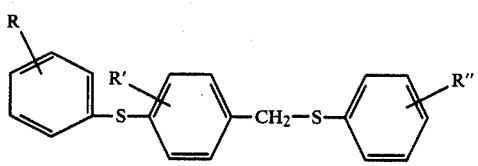

wherein R, R′ and R″ are alkyl groups.

U.S. Pat. No. 3,879,472 (Martin) discloses alkyl sulfides, sulfoxides and sulfones of general formula:

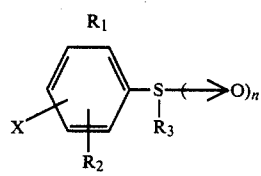

where:
X can be Cl, and
R₁, R₂ and R₃ are alkyl groups.

U.S. Pat. No. 3,686,331 (O'Brien et al) discloses phenyl 3-halopropargyl ethers useful as anti-bacterial and antifungicidal agents.

U.S. Pat. No. 4,108,906 (Anderson) discloses a halogenated aryl compound of general formula:

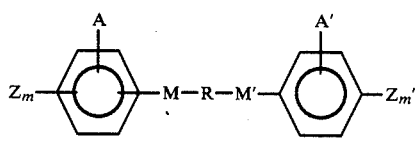

where R can be

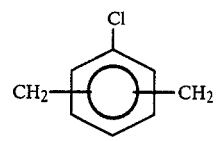

and M and M′ can be sulfur ($Z_m$ can be ClBr), thus making a possible compound of:

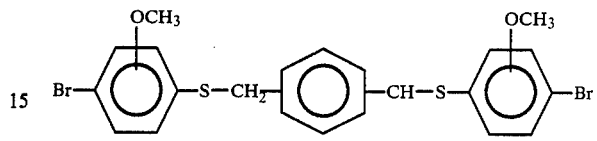

where the A group is —OCH₃

The present invention in its most important aspect relates to novel compositions which are reversible photochromic solids.

The most important practical application of reversible photochromism is information storage by use of lasers.

The state of the art in photo-information storage is the use of tellurium suboxide. Irradiation of this material converts it reversibly to tellurium. The difference between tellurium and its suboxide can then be discerned and thus information can be stored and read (as tellurium). Another state of the art photo storage involves organic photochromics (spirobenzopyrans). These systems have certain drawbacks. Tellurium is highly toxic and the spiropyrans "fatigue" after a few cycles.

We have discovered that molecules having the formula:

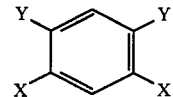

wherein:
X=Cl, Y=

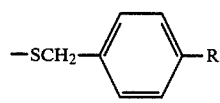

X=Y=

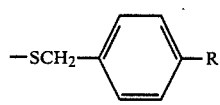

X=Y=

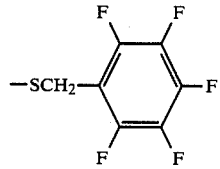

R=hydrogen, halogen such as chlorine, lower alkoxy such as methoxy, or lower alkyl such as methyl, undergo a color change upon irradiation (photochromism). This discovery was applied to the invention of reversible (thermal bleaching) photochromism by a conformational change.

The particular advantage of our system over the state of the art Brown, G. H., Ed. "Photochromism", Wiley Interscience, 1971; Vol. 3 is that no photochemistry occurs during photochromism. Photochemistry requires making and breaking of covalent chemical bonds. This is a relatively high energy process which ultimately becomes irreversible. Our discovery involves simple movement of parts of a molecule; energetically much less demanding and consequently of greater and longer lasting reversibility. It is to be expected that the present invention will be widely adapted by those skilled in the art.

SUMMARY OF THE INVENTION

Briefly, the present invention comprises novel compositions having the formula:

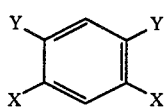

wherein:
X=Cl, Y=

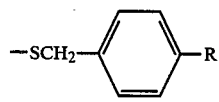

X=Y=

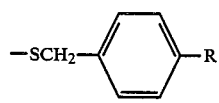

X=Y=

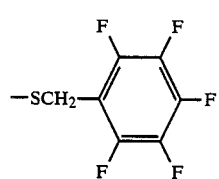

R=hydrogen, halogen such as chlorine, lower alkoxy such as methoxy or lower alkyl such as methyl. The "X" chlorine may be replaced with other halogens such as bromine.

It is an object of our invention to provide new compositions.

More particularly, it is an object of this invention to provide new reversible photochromic solids.

It is also an object of this invention to provide novel methods of making such solids.

These and other objects and advantages of the invention will be apparent from the detailed description which follows.

Turning to the drawings:

FIG. 1 shows electron spin resonance of irradiated 1,2,4,5-tetrakis(benzothio)benzene;

FIG. 2 shows (a) ultraviolet-visible spectrum of 1,2,4,5-tetrakis(benzothio)benzene in $CH_2Cl_2$ solution. There is no absorption in the region 400–900 nm. $\epsilon(268$ nm$)=3\times10^4$. (b) Ultraviolet-visible spectroscoy of 1,2,4,5-tetrakis(benzothio)benezene in the solid state (KBr pellet): (1) white sample; (2) 5 s of exposure to 2550 Å; (3) heating for 1 minute at $\approx 100°$ C.; (4) irradiation for 10 s; (5) heating for 1 minute; (6) irradiation for 10 s; (7) heating for 1 minute; (8) irradiation for 10 s.

Figure 5:
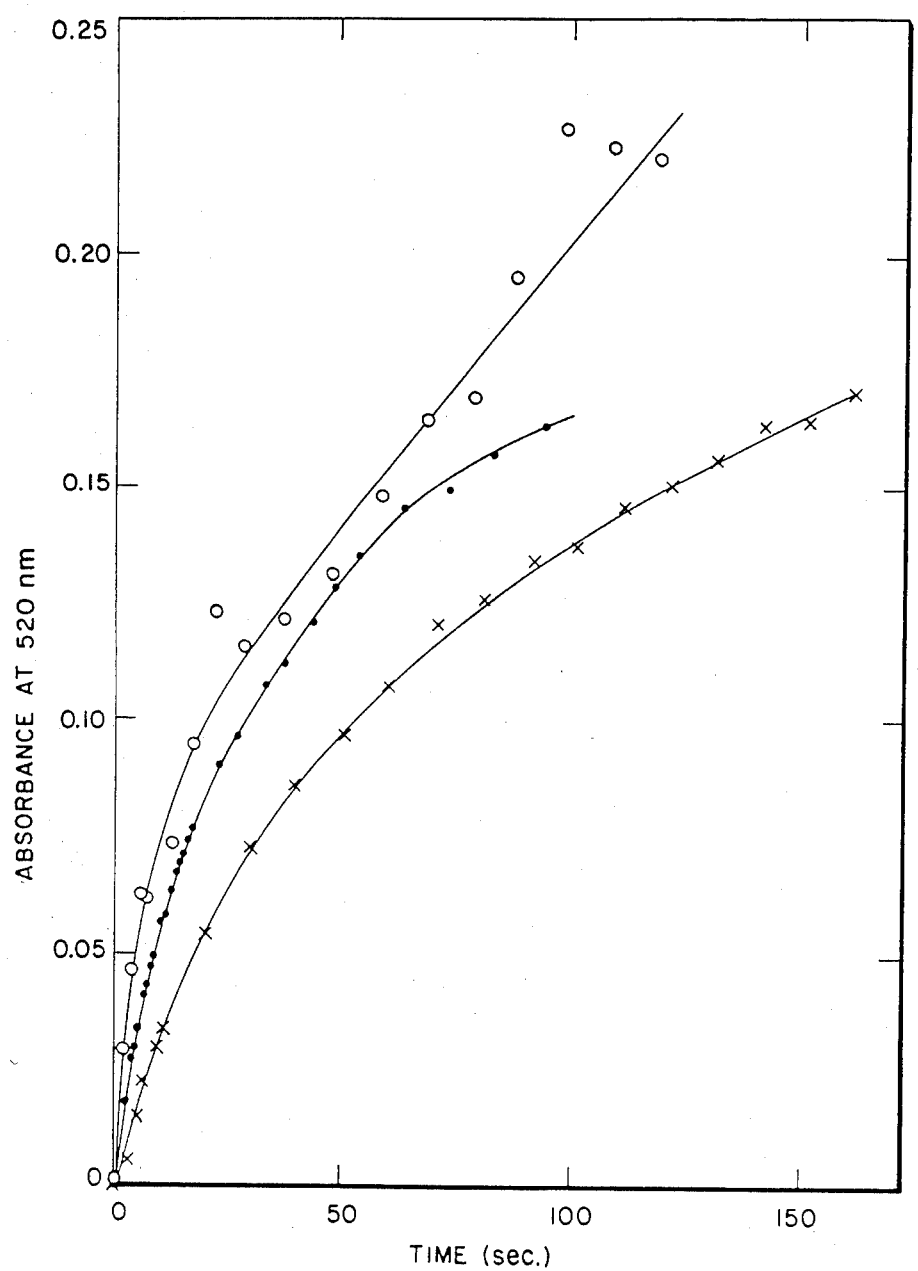

FIG. 5 shows the rate of color development as determined by the rate of appearance of a 520-nm band as a function of time: (•) first coloring cycle of sample A; (x) second coloring cycle of sample A, after bleaching by heating; (o) second coloring cycle of sample B. The figure clearly indicates sample dependence as rate of heating is probably due to inhomogeneity of particle size and dispersion in KBr.

DESCRIPTION OF THE PREFERRED EMBODIMENTS

Preferably, when R is alkoxy or alkyl, the group contains from 1 to about 3 carbon atoms.

The following examples are illustrative only. In the examples, parts and percentages are by weight unless otherwise stated.

One novel route for the synthesis of the novel compounds of this invention is as follows:

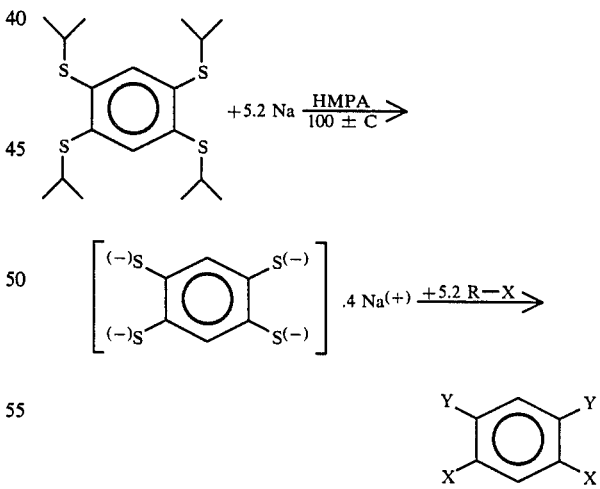

wherein X and Y are as previously defined, and R—X=

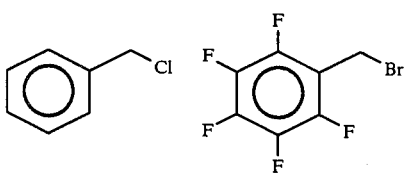

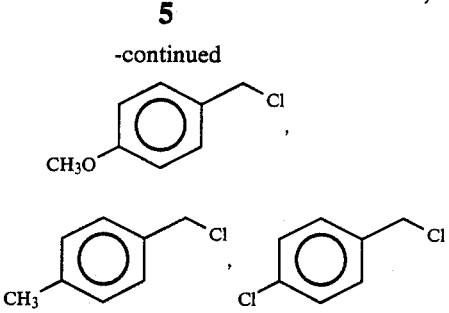

EXAMPLE I

Tetrakis(isopropylthio)benzene (1,87 g, 5.0 mmoles) was dissolved in 30 ml HMPA (hexamethylphosphoramide) under dry, inert atmosphere conditions. The solution was heated to 100° C. and sodium (0.60 g, 26 mmoles) added in small pieces over a few minutes. When all the sodium dissolved (15 minutes-1 hour) the solution was cooled in ice and the electrophile benzylchloride added dropwise over about 5 minutes. The mixture was poured into 300 ml saturated NaCl which precipitated the product. It was filtered, washed with water several times, dissolved in an appropriate organic solvent (CHCl$_3$ or diethylether) and dried over Na$_2$SO$_4$. The solution was filtered and evaporated, giving the crude product, which was crystallized from CHCl$_3$/methanol, ethylacetate or benzene/hexane. The product is 1,2,4,5-tetrakis(benzylthio)benzene.

EXAMPLE II

Tetrakis(isopropylthio)benzene (1,87 g, 5.0 mmoles) was dissolved in 30 ml HMPA under dry, inert atmosphere conditions. The solution was heated to 100° C. and sodium (0.60 g, 26 mmoles) added in small pieces over a few minutes. When all the sodium dissolved (15 minutes-1 hour) the solution was cooled in ice and the electrophile p-methoxybenzylchloride added dropwise over about 5 minutes. The mixture was poured into 300 ml saturated NaCl which precipitated the product. It was filtered, washed with water several times, dissolved in an appropriate organic solvent (CHCl$_3$ or diethylether) and dried over Na$_2$SO$_4$. The solution was filtered and evaporated, giving the crude product, which was crystallized from CHCl$_3$/methanol, ethylacetate or benzene/hexane. The product is 1,2,4,5-tetrakis(p-methoxybenzylthio)benzene.

EXAMPLE III

Tetrakis(isopropylthio)benzene (1,87 g, 5.0 mmoles) was dissolved in 30 ml HMPA under dry, inert atmosphere conditions. The solution was heated to 100° C. and sodium (0.60 g, 26 mmoles) added in small pieces over a few minutes. When all the sodium dissolved (15 minutes-1 hour) the solution was cooled in ice and the electrophile p-methylbenzylchloride added dropwise over about 5 minutes. The mixture was poured into 300 ml saturated NaCl which precipitated the product. It was filtered, washed with water several times, dissolved in an appropriate organic solvent (CHCl$_3$ or diethylether) and dried over Na$_2$SO$_4$. The solution was filtered and evaporated, giving the crude product, which was crystallized from CHCl$_3$/methanol, ethylacetate or benzene/hexane. The product is 1,2,4,5-tetrakis(p-methylbenzylthio)benzene.

EXAMPLE IV

Tetrakis(isopropylthio)benzene (1,87 g, 5.0 mmoles) was dissolved in 30 ml HMPA under dry, inert atmosphere conditions. The solution was heated to 100° C. and sodium (0.60 g, 26 mmoles) added in small pieces over a few minutes. When all the sodium dissolved (15 minutes-1 hour) the solution was cooled to ice and the electrophile p-chlorobenzylchloride added dropwise over about 5 minutes. The mixture was poured into 300 ml saturated NaCl which precipitated the product. It was filtered, washed with water several times, dissolved in an appropriate organic solvent (CHCl$_3$ or diethylether) and dried over Na$_2$SO$_4$. The solution was filtered and evaporated, giving the crude product, which was crystallized from CHCl$_3$/methanol, ethylacetate or benzene/hexane. The product is 1,2,4,5-tetrakis(p-chlorobenzylthio)benzene.

EXAMPLE V

Tetrakis(isopropylthio)benzene (1,87 g, 5.0 mmoles) was dissolved in 30 ml HMPA under dry, inert atmosphere conditions. The solution was heated to 100° C. and sodium (0.60 g, 26 mmoles) added in small pieces over a few minutes. When all the sodium dissolved (15 minutes-1 hour) the solution was cooled in ice and the electrophile pentafluorobenzylbromide added dropwise over about 5 minutes. The mixture was poured into 300 ml saturated NaCl which precipitated the product. It was filtered, washed with water several times, dissolved in an appropriate organic solvent (CHCl$_3$ or diethylether) and dried over Na$_2$SO$_4$. The solution was filtered and evaporated, giving the crude product, which was crystallized from CHCl$_3$/methanol, ethylacetate or benzene/hexane. The product is 1,2,4,5-tetrakis(pentafluorobenzylthio)benzene.

Another novel synthesis route is as follows:

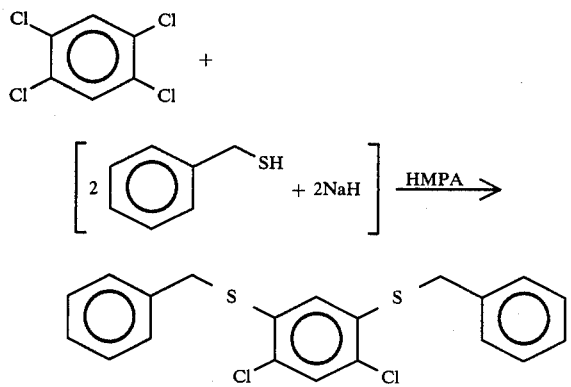

This route is illustrated by the following example.

EXAMPLE VI

Sodium hydride (2.33 g, 97 mmoles) was suspended in 100 ml HMPA in a dry apparatus under inert atmosphere. Benzyl mercaptan 11.4 ml, 12.05 g, 97 mmole) was added dropwise over 30 minutes and the cloudy solution of benzylmercaptide stirred an additional 15 minutes. Tetrachlorobenzene (10.5 g, 48.5 mmoles) was then added as the solid and the mixture heated in an 80° C. oil bath for 1 hour. Cooled and poured into 500 ml saturated NaCl solution, a white precipitate formed. It was filtered, washed with water and methanol and dried in the air. This gave 15.88 g crude product (84% of theoretical) which was crystallized from chloroform or chlorobenzene. The product is 1,5-dichloro-2,4-bis(benzylthio)benzene.

The compound of Example I is a white, crystalline solid, mp 147°–150° C.; soluble $CHCl_3$, EtOAc, acetone, slightly soluble $Et_2O$, insoluble hexane, MeOH. Elemental analysis calcd for $C_{34}H_{30}S_4$: C, 72.04; H, 5.33; S, 22.63. Found: C, 71.94; H, 5.35; S, 22.55. NMR($CDCl_3$), ppm relative to $Me_4Si$) 3.84 (s, 4H), 6.87 (s, 1H), 7.23 (s, 10H). IR (KBr) 3070 w, 3035 w, 1495 m, 1455 m, 1425 m, 690 s, which quickly turns pink when exposed to light, either fluorescent or solar. It can be shown as follows, that this change in color is due to a solid-state process: 1. The infrared spectrum of a KBr pellet before and after coloration is unchanged. 2. Heating of a colored sample pellet returns to its original (white) color. 3. Dissolution of a colored, powered sample causes immediate bleaching; evaporation of the solvent afforded the unchanged compound. 4. Exposure of solutions of the compound in various solvents to ultraviolet or visible radiation reveals no photochromism. 5. Exposure of a sample to ultraviolet or visible light under strictly anaerobic conditions (degassed sample, argon atmosphere) has no deleterious effect on the photochromism.

The above observations indicate (a) that the photochromism is due to a solid-state transformation and (b) that coloration—decoloration is not the result of a (reversible) surface oxidation reaction. Furthermore, the process is a relatively low-energy transformation since it requires only temperatures in the range of 80°–120° C. to effect bleaching.

That all 1-, 2-, 4-, 5-positions on the benzene ring need to be substituted to observe this effect as well as the fact that hexakis(benzylthio) substitution is deleterious can be gathered from examination of Table I.

TABLE I

| Compd | photo-chromicity | color/wavelength,** nm | mp. °C. | Yield,** % |
|---|---|---|---|---|
| o-bis(benzylthio)benzene | no | **** | 73–74 | 30 |
| m-bis(benzylthio)benzene* | no | | 55–56 (lit. 61–62) | 29 |
| p-bis(benzylthio)benzene* | no | **** | 123–125.5 | 50 |
| 1,2,4,-tris(benzylthio)benzene | no | | 124.8–126.0 | 13 |
| hexakis(benzylthio)benzene | no | | 116–118 | 44 |
| 1,2,4,5-tetrakis-(benzylthio)benzene of Example I | Yes | pink/520 | 147.7–150.0 | 30 |

*Results indicated that 1,5-dichloro-2,4-bis(benzylthio)benzene of Example VI is also photochromic.
**Determined from the UV-vis spectrum of the compounds suspended in KBr pellets.
***Isolated yields based on polyhalobenzene.
****Shows no visible color change, but the UV-vis spectrum shows a small absorption oat 440 nm upon exposure to UV.

Electron spin resonance (ESR) and electronic spectroscopy experiments together with a single crystal structure determination were performed on samples of 1,2,4,5-tetrakis(benzothio)benzene.

A sample of pristine 1,2,4,5-tetrakis(benzothio)benzene showed no ESR signal, but pink samples whose color was generated either by exposure to light or X-rays showed a weak, complex signal which increased in intensity and changed shape at 10 K. When a UV-irradiated sample was allowed to remain ("relax") at room temperature for $\approx 72$ h, two closely spaced lines, one at g=2.008 and another at g=2.003 with approximate line widths of 14 and 10 G, respectively were observed at room temperature (cf. FIG. 1). These two g values could correspond to unpaired electrons centered on sulfur and carbon, respectively, and the fact that the line width does not change with temperature implies that the electrons are localized on these atoms. Alternatively, the spectrum could be due to a single species with an anisotropic g tensor. The spectrum of a single crystal was not recorded because the signal was too weak and hence this possibility was not tested. Heating this sample above its bleaching temperatures caused the two sharp signals to disappear. FIG. 2 shows UV-vis spectra of pristine, pink, and "cycled" (bleached) 1,2,4,5-tetrakis(benzothio)benzene in KBr suspension. The first thing to note in this figure is the band at 875 nm in the pristine material. This unusually long-wavelength absorption arises from a solid-state effect because it is absent in solution spectra of 1,2,4,5-tetrakis(benzothio)benzene. It is also clear from FIG. 2 that the absorption responsible for the coloration appears at 520 nm and that "bleaching" results in an increase of overall absorption in the whole region of these spectra.

Figure 3:
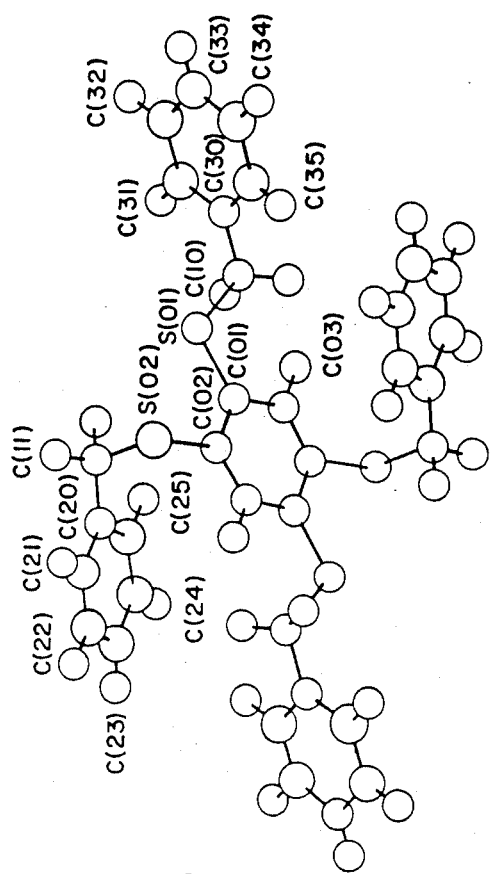
FIG. 3 shows a molecular structure of 1,2,4,5-tetrakis(benzothio)benezene.
Figure 4:
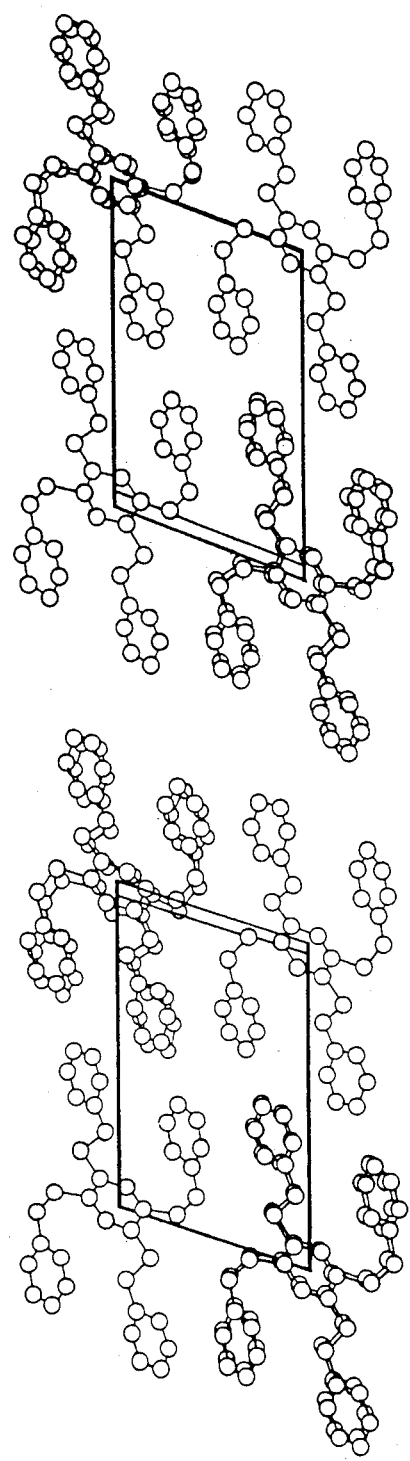
FIG. 4 shows a stereoview of a unit cell depicting molecular packing.

The solid-state structure of 1,2,4,5-tetrakis(benzothio)benezene was determined by a single crystal X-ray diffraction analysis. Crystal data for 1,2,4,5-tetrakis(benzothio)benzene: $S_4C_{34}H_{30}$, $M_r$566.85, triclinic, P1, a=5.358 (6) A, b=10.80 (1) A, c=14.77 (1) A, $\alpha$=106.02(2)°, $\beta$=89.84 (2)°, $\gamma$=117.22 (2)°, V=722.76 $A^3$, Z=1, $D_x$=1.30 gcm$^{-3}$. Diffraction intensities were measured with a modified Picker diffractometer (graphite monochromatized Mo K$\alpha$ radiation). Intensities of 2705 reflections with 2 less than 50° were collected; 1400 were considered observed [I greater than 3 o (1)] and used in refinement. The structure was solved by direct methods (Multan 78) and refined by full matrix least squares to final values of the residuals R=0.047 and $R_w$=0.053. A drawing of the structure depicting the numbering system used is shown in FIG. 3, and a steroview depicting the mode of packing is shown in FIG. 4. Average S-C(sp$^2$) and S—C(sp$^3$) distances observed in the structure are 1.771(4) and 1,830(5) A, respectively. The C—C distances in the benzene ring do not differ significantly from the mean of 1.391 A. The inversion-related C(1) substituents adopt an extended configuration with a C(1)-S(1)-C(10) angle of 103.1 (2)°, while the C(2) substituents fold back to position the phenyl groups above and below the benzene ring. The C(2)-S(2)-C(11) bond angle is 98.6(2)°. The only significant intermolecular interaction is that between extended phenyl groups on the molecules related by the translation a+c. The interplanar spacing between these two parallel groups is 3.54 A, but the overlap involves only the meta and para carbon atoms.

A qualitative study of the rate of coloration (growth rate of the 520-nm band) of 1,2,4,5-tetrakis(benzothio)benzene as a KBr suspension is shown in FIG. 5. As can be seen, the initial rate is quite fast, but 50% "coloration" occurs after ca. 40 s for all runs. "Saturation" seems to be sample dependent but appears to occur at >180 s.

Solid suspensions of 1,2,4,5-tetrakis(benzothio)benzene in poly(vinyl chloride) form tough, free-standing photochromic films which are somewhat more sluggish in their coloration-decoloration cycles than the pristine material. Suspensions of 1,2,4,5-tetrakis(benzothio)benzene in KBr can be cycled at least 16 times without visible fatigue. Upon cycling manually, the base line of the UV-vis spectra rose from 0.4 to 1.0 A at 600 nm in the course of 16 color-bleach cycles. The increase in "background" absorption was observed to be the most pronounced in the first 2-3 cycles. However, the color of the bleached sample remained white. Other similar films may be provided using other organic and inorganic film formers, normally organic polymers which are known in the art.

In conclusion, the present invention provides a new class of photochromic organic solids which appears to be unique. The mechanism has not been fully determined, and applicant does not intend to be bound to any theory. The species responible for the photochromism exhibit an absorption at 520 nm and ESR signals compatible with two radicals: one with an unpaired electron localized on sulfur and another with an electron localized on carbon. While the solid-state strcture implies the possibility of a charge-transfer state, the nature of the colored state is unknown at this time.

Having fully described the invention it is intended that it be limited only by the lawful scope of the appended claims.

I claim:

1. A compound having the generic formula:

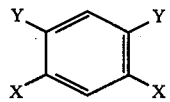

wherein:

X=halogen and Y=

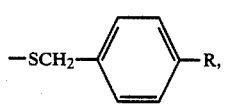

X=Y=

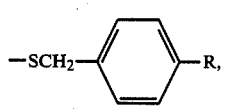

or

X=Y=

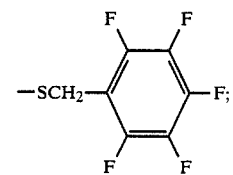

and

R=hydrogen, halogen, lower alkoxy, or lower alkyl.

2. The compound of claim 1 wherein:

X=Y=

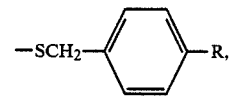

and R=H.

3. The compound of claim 1 wherein:

X=Cl, Y=

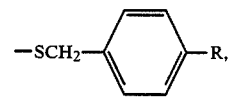

and R=H.

4. The compound of claim 1 wherein:

X=Y=

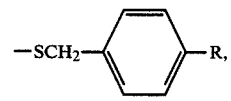

and R=—OCH$_3$.

5. The compound of claim 1 wherein:

X=Y=

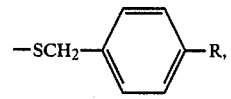

and R=Cl.

6. The compound of claim 1 wherein:

X=Y=

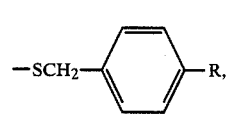

and R=—CH$_3$.

7. The compound of claim 1 wherein:

X=Y=

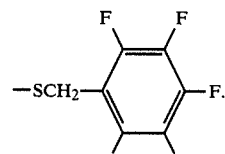

* * * * *